United States Patent [19]

Guy

[11] 3,997,525

[45] Dec. 14, 1976

[54] TETRA-$^{125}$IODO-DI-TYRAMINE OF DIGITALIS DERIVATIVE AND PROCESS FOR MAKING THE SAME

[75] Inventor: Terrance Judd Guy, Minneapolis, Minn.

[73] Assignee: Bio-Tec, Inc., Edina, Minn.

[22] Filed: Jan. 16, 1974

[21] Appl. No.: 433,874

[52] U.S. Cl. .................................. 536/7; 424/182
[51] Int. Cl.$^2$ ........................................ C07J 19/00
[58] Field of Search ................ 260/210.5, 211.5 R; 424/1, 12

[56] References Cited

UNITED STATES PATENTS 3,555,143   6/1967   Axen et al. .......................... 424/12

OTHER PUBLICATIONS

Whistler, R. L., Methods in Carbohydrate Chem. vol. V, Goldstein, I. J., Controlled Regrad. of Polysacch. by Periodate Oxid. Red. & Hydrol, pp. 361–362, Academic Press, New York, (1965).

Hanson, H., Peptides 1972, Wieland, T. Aspects on Synthesis of Biol. Act. Peptides, p. 48, North Holland Publ. Co. (1973).

Hawker, C. D., Radioimmunoassy & Rel. Meth., p. 882, Anal. Chem. vol. 45, No. 11, (Sept. 1973).

*Primary Examiner*—Lewis Gotts
*Assistant Examiner*—Cary Owens
*Attorney, Agent, or Firm*—Williamson, Bains & Moore

[57] ABSTRACT

Tetra$^{125}$Iodo-di-tyramine of digitalis derivatives having the formula:

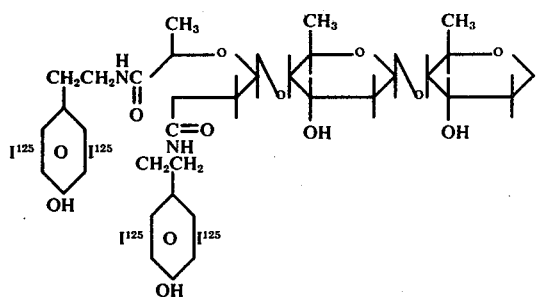

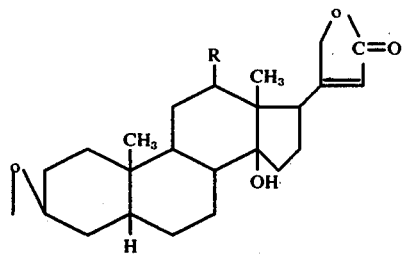

wherein R is hydrogen or hydroxyl; and process for producing the same.

7 Claims, No Drawings

TETRA-[125]IODO-DI-TYRAMINE OF DIGITALIS DERIVATIVE AND PROCESS FOR MAKING THE SAME

BACKGROUND OF THE INVENTION

Digitalis preparations, namely digoxin and digitoxin are used extensively in the therapy of congestive heart failure and certain disturbances of cardiac rhythm. The dosage of digitalis preparations; however, must be carefully adjusted to the needs of these patients so that optimal therapeutic effect is achieved without the development of toxic side-effects. Certain developments have enhanced the physician's ability to adjust the dosage of digitalis preparations to the needs of each patient, and such developments have included; the introduction into clinical use of highly purified cardiac glycosides derived from digitalis leaf; the recognition of the effects of cardiac glycosides on myocardial contractility, conduction in automaticity; and appreciation of the role of electrolyte imbalance in facilitating the development of digitalis toxicity; and a better understanding of the absorption, metabolic fate; and excretion of digitalis based on studies with radioactively labeled cardiac glycosides.

Preparation of isotopically labeled digitalis derivatives allows development of methods for accurate quantitation of nanogram ($1 \times 10^{-9}$) amounts of $^{14}C$ or $^{3}H$ labeled digitoxin and digoxin. The use of radiolabeled digitalis preparations made possible for the first time the direct measurement of cardiac glycosides and their metabolites in the blood and tissues of man and experimental animals. Among many important findings were the observations that serum digoxin concentrations in subjects on usual therapeutic doses were of the order of 1 to 2 ng/ml[4] and for digitoxin approximately tenfold higher.

Several methods or techniques are currently used for determining serum or plasma concentrations of cardiac glycosides, and one such technique is the radioimmunoassay technique. In the radioimmunoassay technique, there is competition between unlabeled molecules present in the fluid to be assayed and a radioactively labeled form of the substance, added in vitro, for a limited number of specific antibody binding sites. At equilibrium, the ratio between antibody bound and free labeled substance is a sensitive indicator of the amount of unlabeled substance originally present in the sample. The radioimmunoassay technique has been used in the measurement of serum levels of both digitoxin and digoxin in the range encountered clinically.

The radioimmunoassay method is the simplest method in current use. It employs whole serum, without the need for an extraction step, and involves the addition of three reagents followed by a single centrifugation step. It is the most rapid; a single serum can be analyzed in one hour and several dozen sera can be assayed in a slightly longer period. Because it is the most sensitive, determinations can be performed on as little as 0.1 ml. of serum. Because of its simplicity (particularly in that no extraction step is required), rapidity, and sensitivity, the radioimmunoassay method is the most convenient for routine clinical determinations of serum concentrations of digoxin and digitoxin. Its principal disadvantage is that it employs liquid scintillation counting, with the resultant problems of quenching and chemiluminescence, problems that have been overcome by the use of radioiodinated digitalis derivatives.

The cardiac glycosides are all relatively small molecules with molecular weights in the 500–1000 range and are too small to be immunogenic by themselves. Therefore, in order to obtain antibodies to cardiac glycosides, it is necessary to conjugate these pharmacologic agents as haptens to antigenic protein carriers. For this purpose, periodate oxidized glycosides have been coupled to albumin carriers to form synthetic glycoside-protein conjugates. Alternatively, the 3-O-succinyl derivatives of digitoxigenin and digoxigenin, the cardioactive steroidal aglycone portions of the corresponding glycosides, lacking the 3 digitoxose residues have been conjugated to albumin carriers by carbodiimide and mixed anhydride methods. Rabbits and other animals immunized with such conjugates formed antibodies to the protein carrier and also formed antibodies to the glycoside hapten. Antibodies to digoxin produced in this manner have been shown to have a high affinity and great specificity for this glycoside. For example, antidigoxin antibodies bind digoxin at least twenty times more effectively than they bind digitoxin, although digitoxin differs structurally from digoxin only in the absence of a single hydroxyl group at the C-12 position.

In the radioimmunoassay procedure, the non-radioactive glycoside will compete with the radioactive labeled glycoside for combining sites on antidigitalis antibodies.

When varying quantities of unlabeled digitalis are mixed with a standard amount of radio labeled glycoside, the amount of radioactivity bound by a standard amount of antibody will decrease as increasing amounts of unlabeled glycosides are added. A standard curve can then be constructed from which the concentration of digitalis in a given patient serum can be determined on the basis of the decrease that it causes in the binding of radioactive glycoside by a specific antibody.

In certain clinical situations, it is necessary to obtain digoxin results as quickly as possible. The unavailability of the history of digoxin dosage, and in cases of malabsorption and fluctuating renal function, are typical clinical situations that arise in which rapid results are required. It has been determined that quantitation of the cardiac glycosides in serum or plasma is most conveniently accomplished through radioimmunoassay. This assay method is the most rapid, precise sensitive and specific, and at the same time can readily cope with a large number of patient samples. The use of iodinated digoxin further increases assay sensitivity, shortens counting time, and eliminates the problems with the liquid scintillation counting of beta emitting $^{3}H$ (tritiated) glycosides. Thus, the major practical contribution of the use of iodinated cardiac glycosides is a combination of counting reliability and assay speed.

There are commercially prepared radioiodinated derivatives of digoxin and digitoxin for use in radioimmunoassay tests, but these prior art radioiodinated digitalis derivatives have certain disadvantages. The principle disadvantage of these prior art compounds is the steric hindrance involved during the antigen-antibody reaction.

SUMMARY OF THE INVENTION

It is therefore a general object of this invention to provide a radioimmunoassay compound, tetra-[125]iododityramine derivative of digitalis and process of making the same. Tetra-$^{125}$Iodo-di-tyramine derivatives of digitalis readily combine with their specific antibodies and are therefore highly effective for use in radioimmunoassay tests for determining levels of digoxin and digitoxin in patient serum. It has also been found that the disclosed process for synthesizing tetra-$^{125}$Iodo-di-tyramine derivatives of digitalis (digoxin and digitoxin) is rapid and efficient when compared to prior art processes for producing radioiodinated digitalis derivatives.

Therefore, as pointed out above, the primary application of a radioiodinated digitalis molecule is to evaluate the blood levels of digoxin or digitoxin, thus providing the physician a valuable tool in the determination of a proper dosage regimen in a given patient. However, by no means is such a molecule limited in scope to the "dosage-toxicity" problems. Other areas of potential application lie in the use of blood level measurements to extend our understanding of the clinical pharmacology of digitalis glycosides in various disease states. For example, the digoxin radioimmunoassay has been employed to study the absorption of oral digoxin in patients with malabsorptionsyndromes. The metabolism and excretion of digitoxin is more complex and less well understood than of digoxin; methods currently in use should help to define the roles of renal and hepatic function in the metabolism and excretion of digitoxin. Problems such as variability in gut absorption and nonrenal excretion of digoxin deserve careful study. Largely unexplored, as yet, is the quantitative relationship between blood levels of chronically administered cardiac glycosides and myocardial inotropic response to these drugs. Clinical studies combining contractility measurements and blood glycoside levels would be of considerable interest. The radioiodinated digitalis derivative will undoubtedly find its place at the fore in the armamentaria used to solve these and other related problems.

DESCRIPTION OF THE PREFERRED EMBODIMENT OF THE INVENTION

The first requirement for an acceptable radioimmunoassay is the preparation of a highly purified antigen that can be radiolabeled or "tagged" without producing any loss in immunoreactivity. In the case of the cardiac glycosides, this poses a very unique and difficult problem in that these glycosides do not lend themselves inherently to radioiodination. A suitable derivative must therefore, be chemically synthesized from the parent glycoside which will prove applicable to the radioimmunoassay of serum digitalis levels. It follows that the stepwise chemical reactions involved in the preparation of said derivative must be of such a nature that:

1. the chemical reactions be relatively specific and not broad in spectrum—thus resulting in unknown alterations of the parent compound which might alter immunoreactivity, 2. the antigenic differences between digoxin and digitoxin be preserved (the presence of a secondary hydroxyl group at the C-12 position of digoxin which is absent in digitoxin), 3. no alteration of the antigen specific aglycone ring portion of the digitalis molecule, 4. the derivative be of a high radioactive specific activity thus permitting the use of extremely small quantities of the derivative in the assay procedure (a strong tenet in the theory of the principles of competitive protein binding assays as well as for efficiency and economy), 5. the separation of the radiolabeled derivative from the nonlabeled derivative be easily and quickly facilitated, 6. the derivative be relatively stable (discounting radioactive decay which is an assumed constant) that is not subject to gross alteration of immunoreactivity due to environmental hazards such as air oxidation, 7. the prepared derivative be relatively soluble in the standard biological fluid media—such as water, buffered salt solutions, serum proteins, etc., 8. the non-antibody bound derivative in the radioimmunoassay prove separable from the antibody bound derivative through the standard steroid separation procedures—adsorption on dextran or gelatin coated charcoal, 9. the production of said derivative be facile, practical, economical and suitable for large scale clinical and industrial application, 10. the derivative competes efficiently and effectively with standard and patient cardiac glycosides for the respective specific antibody and that its use provide an accurate, reliable, efficacious determination and quantitation of the digitalis concentration ranges encountered clinically.

In preparing tetra-$^{125}$Iodo-di-tyramine digoxin (or digitoxin), digoxin (or digitoxin) is oxidized, preferably by periodate oxidation, to cause glycol cleavage of the a-glycol groups. Since digoxin is the more commonly used digitalis derivative for therapeutic purposes, only the synthesis of tetra-$^{125}$Iodo-di-tyramine digoxin will be disclosed in detail. It is felt that it is unnecessary to disclose a detailed synthesis of tetra-$^{125}$Iodo-di-tyramine digitoxin, since the digitoxin and digoxin are structurally similar.

Both glycosides consists of aglycones and glycosidic portions. The two molecules differ only in one position: digoxigenin, the aglycone of digoxin, has -OH group at C-12 position in the steriod ring; this hydroxyl group is absent in digitoxigenin.

During periodate oxidation, each a-glycol group consumes one molecular portion of periodate, and under given conditions, the rate of reaction is dependent principally upon the steriochemistry of the a-glycol group. Periodic acid and its sodium and potassium salts are commercially available, and their use depends on the pH of the reaction solution. Sodium metaperiodate is most soluble in neutral and weakly acidic aqueous solutions (unbuffered aqueous solutions of the sodium salt have a pH of about 4) but is insoluble in alkaline solutions. However, potassiumdimesoperiodate (prepared from the metaperiodate) is soluble in alkaline aqueous solutions. For solutions of pH less than 3, periodic acid is used.

In the oxidation of most carbohydrates, water is the principle solvent used and is the medium in which periodate oxidation is most easily effected. However, in the case of digoxin (or digitoxin), water insoluble compounds, aqueous mixtures of alcohols, dioxane or acetic acid may be used, but it should be noted that in these solvent mixtures the oxidation is considerably slower than water. Since periodate solutions decompose at a measurable rate in sunlight, all oxidations must be carried out in the dark.

Room temperature is generally used since the amount of nonspecific oxidation increases at higher temperatures. Temperatures lower than room temperatures are occasionally necessary to prevent hydrolysis of acetal linkages in acid solution or to suppress non-specific oxidation. It has been shown that glycol cleavage occurs more readily the greater the excess and the higher the concentration of periodate. The concentration range used is generally 0.01 M to 0.1 M; concentrations greater than these can promote nonspecific oxidation.

At constant pH and temperature, the rate of oxidation is mainly dependent on the steriochemistry of the glycol molecule. The reaction time may vary from a few seconds, with simple glycols, to several days for highly sterically hindered glycols. In the case of digoxin (or digitoxin), one hour appears to be a sufficient amount of time to accomplish the oxidation of the terminal carbohydrate glycol moiety. It should be pointed out that with only a very slight excess of periodate, the reaction time will be longer than in an analytical determination using a large excess of periodate. Buffer solutions may be used, but it is preferred that the use of buffers be avoided since the use of buffers necessitates the removal of several ions from the solution at the end of the reaction.

Periodate oxidation of digoxin forms hemialdal digoxin as follows:

ally as a hemialdal or internal hemiacetal. Spectroscopic evidence has also been found for the cyclic intermediate further supporting the view that this intermediate is formed by electrophilic attack on the glycol.

Removal of the periodate and iodate ions is accomplished through chemical precipitation with barium chloride. However, barium hydroxide, lead acetate, and lead nitrate may also be used to precipitate the periodate and iodate ions although strontium hydroxide is a more widely used alternative to barium chloride. Other methods which may be used to remove periodate and iodate ions are: the use of ion exchange resins with subsequent concentration and extraction employing a suitable solvent, equilibrium dialysis, or by lyophilization of the oxidation solution followed by solvent extraction.

The digoxin hemialdal is then converted to digoxin di-carboxylic acid, preferably by Tollen's reagent (ammonical silver nitrate solution). Oxidation of aldehydes to carboxyl groups is typically accomplished by silver oxide (as an analytical reagent) usually prepared from silver nitrate and sodium hydroxide. This reagent is especially useful when other oxidizable groups are present and advantage can be taken of the fact that Tollen's reagent does not attack carbon-carbon double bonds. For example, almost quantitative yields of un-

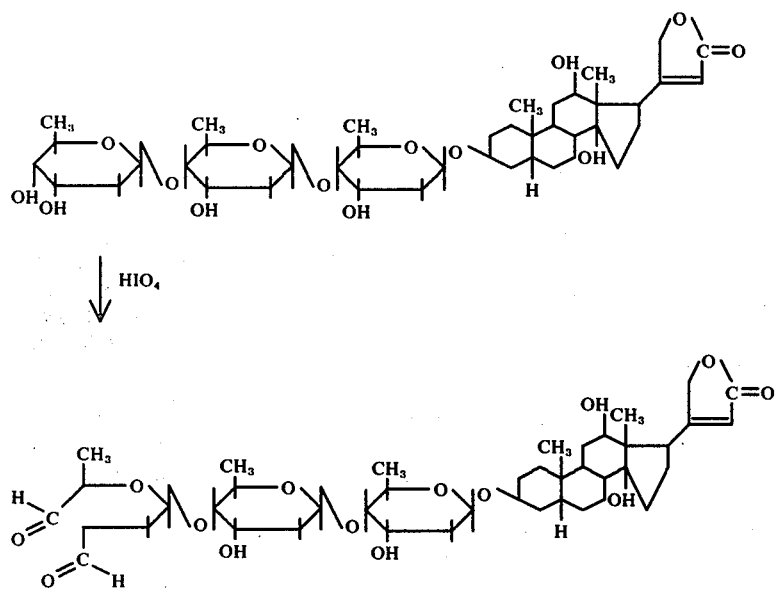

Other agents which will convert 1–2 glycols to carbonyl products in good yield include lead tetraacetate, aryl iodosoacetate, manganic pyrophosphate and sodium bismuthate. Lead tetraacetate behaves similarly to periodic acids and its sodium or potassium salts. However, with lead tetraacetate, the rate of oxidation varies tremendously with the glycol, cis isomers being, in general more rapidly oxidized than the corresponding trans compounds. Oxidations of glycols by lead tetraacetate are catalyzed by both acids and bases. Lead tetraacetate is considered to be more vigorous and less selective than periodic acid. Aryl iodosacetates form another class of oxidants which are similar to lead tetraacetate but cause somewhat less rapid oxidative cleavage of glycols. It should be noted that no periodate oxidation product has been isolated directly from an oxidation solution as the free di-aldehyde, but ususaturated carboxylic acids have been obtained from the corresponding unsaturated aldehydes by oxidation with Tollen's reagent. Oxidation by silver ion prefers an alkaline medium, and to prevent precipitation of the insoluble silver oxide, a complexing agent is added. Tollen's reagent, an ammoniacial silver nitrate solution, is prepared by precipitating silver oxide from a 5% solution of silver nitrate by the addition of 10% sodium hydroxide. A 2% solution of ammonia hydroxide was added until the silver oxide just dissolved. The reagent must be freshly prepared for use, since it has a tendency to deteriorate on standing, forming an explosive compound. Thus any excess reagent must be discarded immediately and any silver mirrors should be dissolved in nitric acid and the solution discarded. Conversion of the digoxin hemialdal by Tollen's reagent to digoxin di-carboxylic acid is as follows:

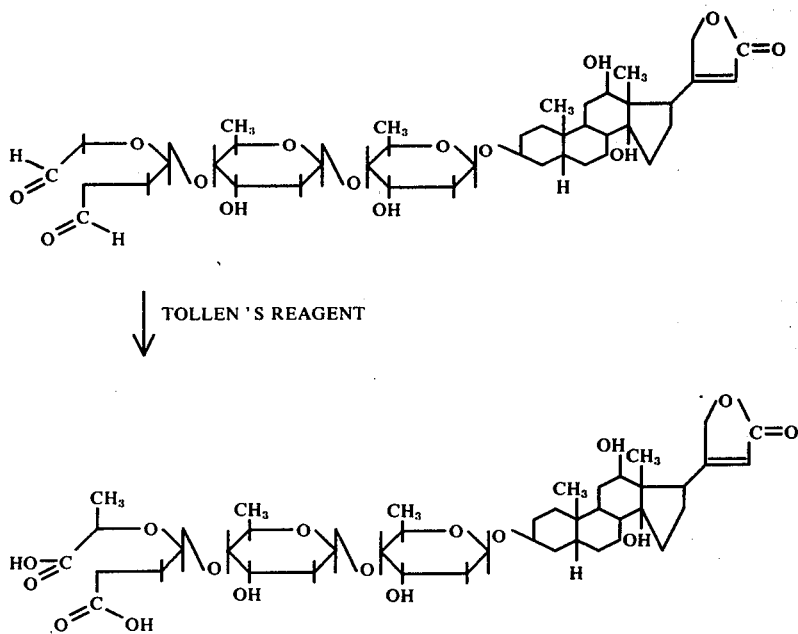

Other reagents that may be used to convert the digoxin (or digitoxin) hemialdal to its corresponding di-carboxylic acid are: Fehling's solution, an alkaline Copper II solution containing tarate to complex with the copper ion to prevent precipitation of the hydroxide; and Benedict's solution, which is a copper citrate complex. Argentic or Silver II ion which is a considerably more powerful oxidant than Silver I, has usually been employed as the picolinate in water, dimethylsulphoxide, or dimethoxyethane. It should also be pointed out that it appears feasible to accomplish oxidation of aldehydes with an alkaline solution of potassium mercuric oxide, which is a modification of Nessler's reagent. Aliphatic aldehydes are smoothly oxidized by bromine in aqueous solution, and iodine in base has also been used to successfully oxidize aliphtic aldehydes. N-bromosuccinimides have been used to convert aldehydes to acids. In addition, aldehydes are converted to their corresponding acids by Mercury II oxide, Vanadium V, Chromium VI, Manganese II, permanganate in acid or alkali, manganese dioxide, Cobalt, Cerium, and Nickel peroxide in alkaline solution.

It is further pointed out that oxidation of aldehydes to carboxylic acids can also be accomplished with nitric acid. Aldehydes also readily undergo oxidation to the corresponding acid on standing in air. Such oxidation of aldehydes generally proceeds by a chain mechanism. Auto-oxidation of aldehydes may be initiated by several catalysts, including metal ions, such as iron or cobalt, which convert the aldehyde to a radical by direct electron transfer. Radical production in auto-oxidation may also come from heat, light or ionizing radiation. Benzoyl peroxide, benzenediazoacetate, and lead tetraacetate, have been used as catalysts in aldehyde auto-oxidation. Organic peroxy acids have also been used in the oxidation of aldehydes to carboxylic acids and are suggested as general reagents for this purpose. Aldehydes are rapidly oxidized to the acids by ruthenium tetroxide. However, it is preferred that Tollen's reagent (ammoniacial silver nitrate solution) be used in the conversion of digoxin (or digitoxin) hemialdal to digoxin (or digitoxin) by carboxylic acid.

The next step of my synthesis involves formation of a peptide bond between the phenolic amine, tyramine, and the di-carboxylic acid moiety of digoxin. In the preferred embodiments, 1-cyclohexyl-3-(2-morpholinoethyl)-carbodiimide-metho-P-toluene sulfonate is used for coupling tyramine to digoxin di-carboxylic acid. In this synthesis, a single reaction serves to convert both the reacting carboxyl and reacting amine to the peptide bond. Although 1-cyclohexyl-3-(2-morpholinoethyl)-carbodiimide-metho-P-toluene sulfonte is preferred, other carbodiimides may also be used to convert the reacting carboxyl and reacting amine to a peptide bond. Other soluble carbodiimides may also be used such as N-ethyl-N' (2-morpholinylethyl)-carbodiimide-metho-p-toluene sulfonate. Other carbodiimides include N,N'-dicyclohexyl carbodiimides N-ethyl-N'-(2-morpholinyl-ethyl)-carbodiimide and N-(3-dimethylamino propyl)-N'-T-butyl carbodiimide. The formation of the di-tyramine digoxin from digoxin di-carboxylic acid with tyramine (nucleophile) and 1-cyclohexyl-3-(2-morpholinoethyl)-carbodiimide-metho-p-toluene sulfonate is as follows:

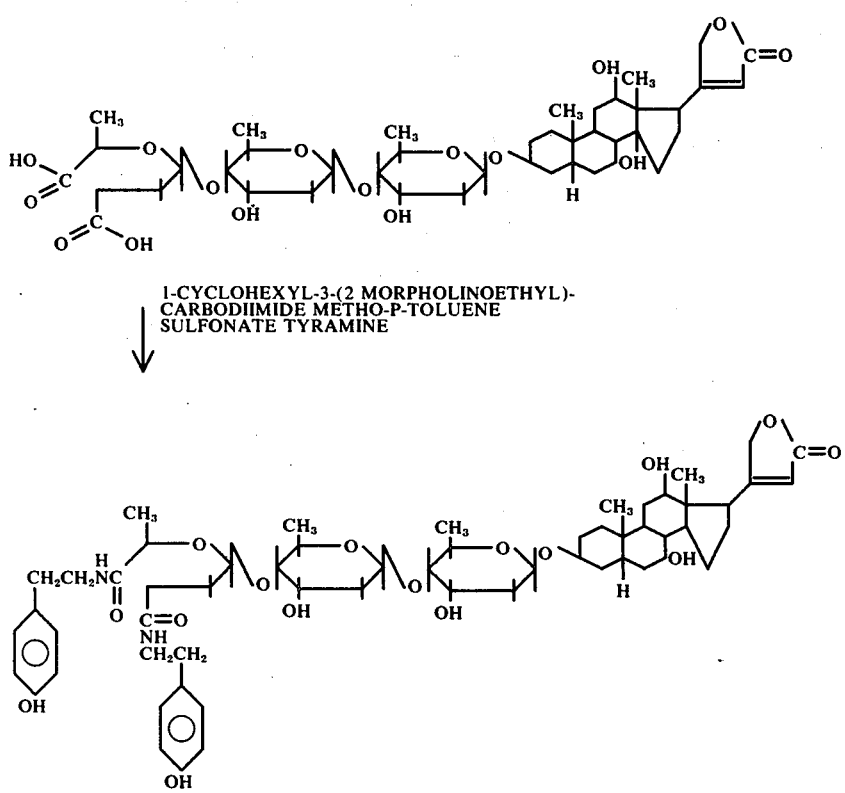

The use of carbodiimides as a coupling reagent and especially N,N'-dicyclohexylcarbodiimide, is based upon the high reactivity of carbodiimides since this characteristic assures that the desired coupling reactions will proceed smoothly, usually to the completion of the acylation within a short time. In the coupling reaction, the probable mechanism involves the formation of an intermediate O-acylisourea. These highly reactive intermediates either slowly hydrolyze, condense with amines to yield corresponding amides, or condense with other nucleophiles to give a large number of different carboxylate derivatives. The two C=N bonds make the central carbon atom very reactive towards nucleophiles particularly in the presence of an acid. The resulting adduct containing the grouping —CO—O—C=NR is analogous to an anhydride and reacts readily with the amino groups. Although the high reactivity of carbodiimides involves some disadvantages, the advantages far outweigh these disadvantages and this is the reason why the carbodiimides are preferred as the coupling reagent.

Other coupling methods and coupling reagents may also be used such as acid chlorides. It has been found that acid chlorides are exceptionally reactive towards nucleophiles and peptide-bond formation occurs readily, but chloride ion is such a good leaving group that N-carboxyanhydrides are formed from benzyloxycarbonyl-protected acid chlorides.

Another coupling system which may be used is azides wherein conversion of an acid into an azide can be accomplished under relatively mild conditions. Azides, although not so reactive as chlorides are sufficiently reactive for peptide-bond formation to occur smoothly without the competing reaction leading to the N-carboxyanhydride.

Mixed anhydrides are readily formed by displacement by the nucleophilic carboxylate anion on an acid chloride. A typical example is the reaction with ethyl chloroformate, triethylamine being added to generate the carboxylate ion. Reaction of an amino group with the resulting mixed anhydride occurs smoothly.

Activated esters are also useful as coupling systems. Although alkyl esters are not very reactive towards amines, aryl esters. particularly those with electron-attracting substituents react readily.

The selection of tyramine as a nucleophile in its carbodiimide catalyzed coupling to digoxin (or digitoxin) di-carboxylic acid is based upon several considerations. In this respect, it should be pointed out that tyramine is commerically available with good purity and economy. The solubility characteristics of tyramine are such that the uncoupled tyramine may be easily removed from the reaction mixture along with the cyclohexyl ureas and various salts encountered. It is further pointed out that tyramine is classified as a primary amine and is endowed with a high nucleophillic reactivity. It must be noted, however, that secondary amines are also nucleophillic in nature, however, to a lesser degree; with tertiary amines failing to react. Finally, the phenolic character of tyramine also lends itself well to the radioactive iodination procedure which is the final step involved in the synthesis of tetra-$^{125}$Iodo-di-tyramine digoxin.

In the radioiodination of di-tyramine digoxin (and digitoxin) it is important that the resulting radioactive preparation have a high specific activity with good stability and unimpaired immunoactivity. It is pointed out that each digoxin (or digitoxin) derivative has the potential to accept not just two iodide moietys per derivative, but four iodide moietys.

Although [125]-iodine and [131]-iodine each possesses distinctive advantages for use in radioiodination, [125]-iodine is preferred. In this respect, it is pointed out that [125]-iodine has a longer half life (60 days) than does [131]-iodine (8 days). In addition, [125]-iodine has a higher counting efficiency under certain conditions, can be produced practically carrier-free, and is relatively inexpensive. [125]-Iodine also has a lower gamma energy than does [131]-iodine and the absence of betaradiation diminishes the potential for auto destruction of the labeled antigen.

Oxidation of the labeled NaI is generally performed by using excess chloramine T which results in a high specific radioactivity with a low hazard to health. To minimize preparation damage to the molecule, both reaction time and the amount of oxidizing agent must be limited. While the favored exposure time ranges from less than ten seconds to four minutes, the chloramine T concentration in the specific antigen being labeled must also be considered. For example, experience has indicated that conditions were optimal with 4 ug of chloramine T per ug of steroid with a reaction time of two minutes.

Iodination is usually carried out at room temperature at a pH of 7.5 in a phosphate buffer medium that ranges in concentration from 0.05 to 0.5 Molar. Iodination may take longer to complete at lower temperatures or at a higher pH. The reaction is usually stopped with excessive sodium metabisulphite. The tagged antigen may be damaged during or soon after the iodination reaction and the extent of the damage may vary, not only among various antigens being labeled, but among different lots of the same antigen.

To decrease potential damage caused by the isotope, the chloramine T, or the metabisulphite, the labeled antigen must be separated as quickly as possible from the labeled and unlabeled degraded antigen, the mineral salts and the unreactive iosotopic material. In the case of the dityramine digoxin, (or di-tyramine digitoxin) it was possible to omit the metabisulphite and purify the material immediately. This was accomplished by thin layer chromotography on silica gel impregnated paper run in a benezene-ethanol 3-A- (90:10) solvent system.

Various techniques are available for the separation and purification of tagged antigens. Absorption chromatography on powdered cellulose has been used to eliminate mineral salts. The free iosotope remains in the column while the labeled antigen passes through with the eluting solvent. Other purification techniques may be used, including dialysis, chromato-electrophoresis, gel filtration (using a molecular sieve) or ion exchange chromatography. These last mentioned methods employ the use of cross linked dextrans (Sephadexes or Bio-Gels) DEAE or QAE powdered celluloses, Dowex resins, other anion exchange resins. Inorganic iodine resins have also been used to adsorb the unreactive radioiodine ions.

Chloramine T and $Na^{125}I$ is reacted with di-tyramine digoxin to form tetra-$^{125}$Iodo-di-tyramine digoxin as follows:

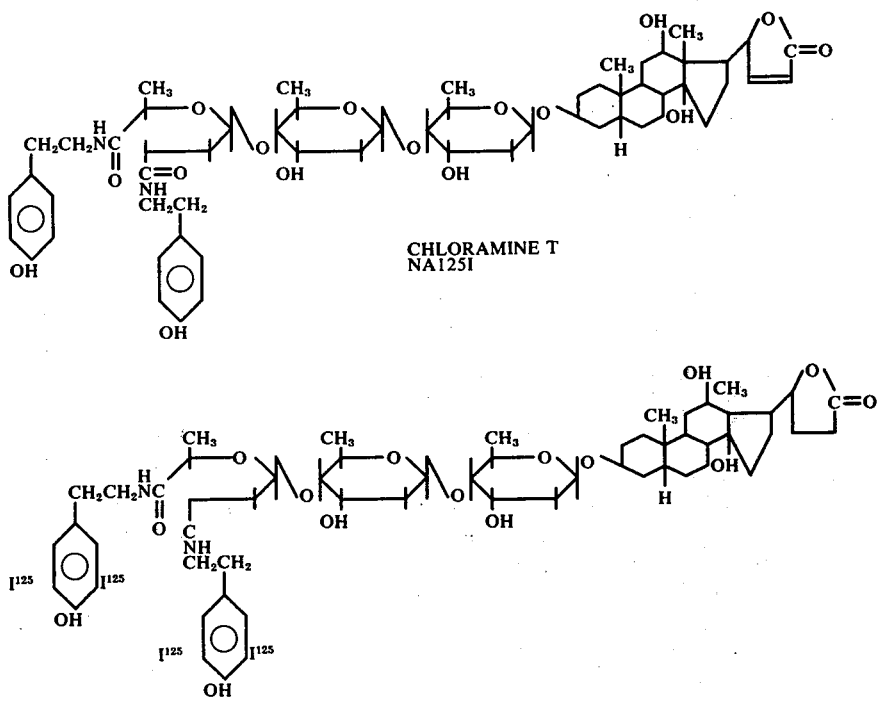

The following is an example of the synthesis of tetra-$^{125}$Iodo-di-tyramine digoxin.

EXAMPLE 225 mg of crystalline digoxin were dissolved in 20 ml of hot ethanol and dioxane, (80:20) 10 ml of a .1 M solution of sodium-meta-periodate was added dropwise. The reaction was allowed to proceed with stirring, in the dark and at room temperature for one hour. A 1.0 M solution of barium chloride was added to the reaction mixture to remove the excess sodium-meta-periodate. A white flocculant precipitate resulted and was subsequently centrifuged and the supernatant decanted. The addition of small aliquots of the barium chloride solution was continued until the reaction mixture supernatant revealed no further precipitation upon standing.

Tollen's reagent was prepared by precipitating silver oxide from a 5% solution of silver nitrate by the dropwise addition of 10% sodium hydroxide. A 2% solution of ammonium hydroxide was added until the silver oxide (reddish-brown)precipitate) just dissolved. (The reagent must be freshly prepared before each use with excess reagent being disposed of immediately.) 10 ml of the freshly prepared Tollen's reagent was added to the periodated digoxin, the reaction mixture was covered, and oxidation allowed to proceed until the formation of a silver mirror which appeared in usually two days at room temperature.

The pH of the reaction solution was adjusted to 6.0 with the aid of 6N HCl. 5 ml of 1.0 M solution of tyramine dissolved in hot ethanol and 5 ml of 1.0 M solution of 1-cyclohexyl-3-(2-morpholinoethyl)-carbodiimide metho-p-toluene sulfonate in water was added with the reaction allowed to proceed overnight at room temperature with stirring. The following morning, the entire reaction mixture was poured onto a piece of Whatman Filter Paper No. 1 and allowed to dry. The filter paper was cut into small squares and eluted with acetone. (This procedure provided separation of the various salts, cyclohexylureas, and unreacted tyramine.) The acetone eluate was then subjected to thin layer chromatography on silica gel sheets 20×20 cm size in benzene-ethanol 3-A-(90:10). Spotted along with samples of the acetone eluate were digoxin, tyramine, a sample of an aliquot of the reaction mixtures following barium chloride treatment and the Tollen's oxidation step. Upon development in the benzene ethanol, the chromatogram was subjected to sulphuric acid charring and nitroso-napthol in ethanol for viewing under U.V. light. (Sulphuric acid and nitroso-napthol being steroid and phenolic indicators respectively.) Using the digoxin and tyramine migration as references, the migration of the reaction products were noted and Rf values approximated: digoxin 0.5; tyramine 0.3; dialdehyde digoxin 0.8; di-acid digoxin 0.7; di-tyramine digoxin 0.4; and 0.6 (two spots for the di-tyramine digoxin were visualized, probably confomers.) The acetone eluate was then subjected to preparative thin layer chromatography employing the 90:10 benzene-ethanol solvent system. The origin was located 3 cm from the bottom of the TLC-SG sheet with the solvent front allowed to migrate 18 cm. (The time for chromatogram development at room temperature was approximately 20 minutes.) Upon development of the chromatogram, the silica gel TLC sheet was divided into 15 horizontal 1 cm strips. (Beginning with the origin and ending with solvent front.) Strips 6–10, (that area corresponding to $R_f$ values of 0.4 and 0.7) the strips indicating the di-tyramine digoxin derivative, were eluted in 20 ml of ethanol 3-A.

The ethanol eluate was concentrated to 10 ml and 20 ul of the approximately 10 ug/ml solution of the di-tyramine digoxin were added to 200 ul of ethanol 3-A. 20 ul of carrier free Na$^{125}$I in NaOH possessing 80–140 mCi/ml was introduced followed by 10 ul of a 4 µg/ml solution of chloramine T. The reaction was allowed to proceed for exactly two minutes. The reaction was immediately diluted with 1.0 ml of ethanol and subjected to preparative thin layer chromatography in benzene-ethanol 3-A. 90:10) Unreacted Na$^{125}$I remained at the origin with the tetra-$^{125}$Iodo-di-tyramine digoxin exhibiting an approximated $R_f$ value of between 0.7 and 0.9. Again, these strips were cut and eluted in ethanol 3-A. The eluate was tested for antibody binding with rabbit antidigoxin antiserum. The antibody bound approximately 85% of the total counts with the unbound digoxin derivative separated by adsorption on dextran coated charcoal, with a subsequent antibody titer towards the digoxin derivative determined to be 1:40,000. Further attempts to increase the percentage of the derivative bound by the antibody by increasing the purity of the eluate through thin layer chromatography and other methods proved unsuccessful. The ethanol tetra-$^{125}$Iodo-di-tyramine digoxin was diluted in water; 0.1% acetic acid, 0.1% Na azide to 20,000 cmp (via liquid scintillation determination on the Searle Radiographic Iso-Cap 300) and refrigerated for subsequent use in the radioimmunoassay for quantitation of digoxin serum levels.

The tetra-$^{125}$Iodo-di-tyramine digoxin (or digitoxin) is especially useful as a radioimmunoassay agent in determining the levels of digoxin (or digitoxin in a patient's serum or blood. As pointed out above, if one mixes varying quantities of unlabeled digoxin (or digitoxin) with a standard amount of radiolabeled glycoside, the amount of radioactivity bound by a standard amount of antibody will decrease as increasing amounts of unlabeled glycosides are added. The radioimmunoassay method may be diagrammatically represented as follows:

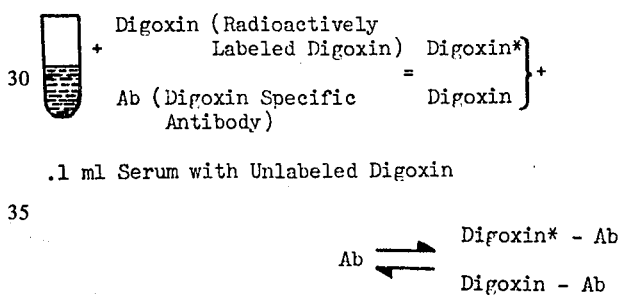

The amount of antibody bound digoxin* (digoxin*-Ab) present at equilibrium is determined by the quantity of unlabeled digoxin present in the sample. Thereafter, the bound digoxin is separated from the free digoxin. The separation of bound from the free digoxin may also be diagrammatically represented as follows:

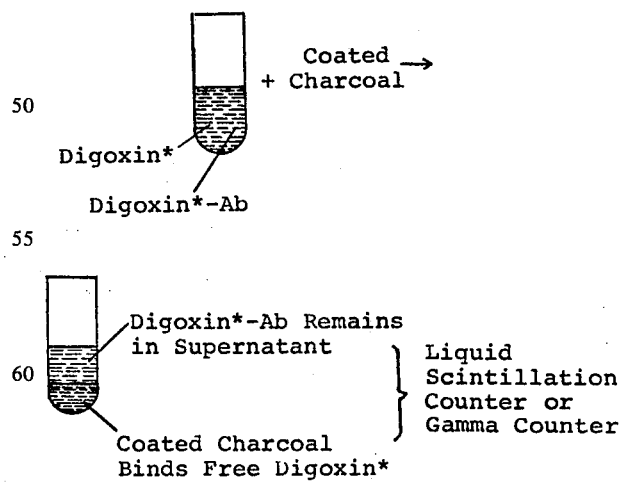

Dextran-coated charcoal selectively binds free digoxin*; antibody-bound digoxin* in the supernatant after centrifugation is then counted. A standard curve can then be constructed from which the concentration of digoxin (or digitoxin) in a given patient's serum can be determined on the basis of the percent inhibition in the binding of the radioactive cardiac glycoside.

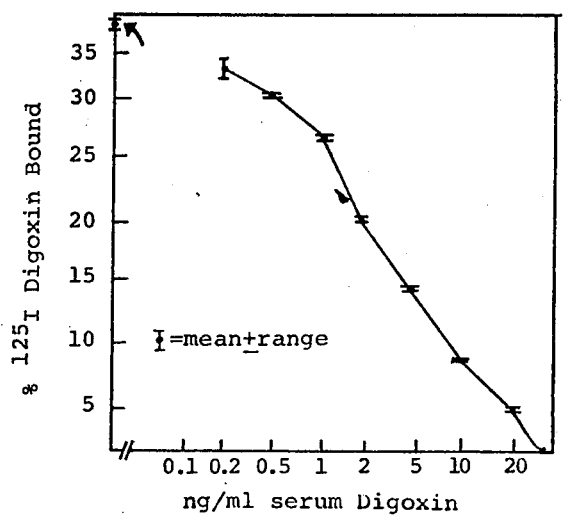

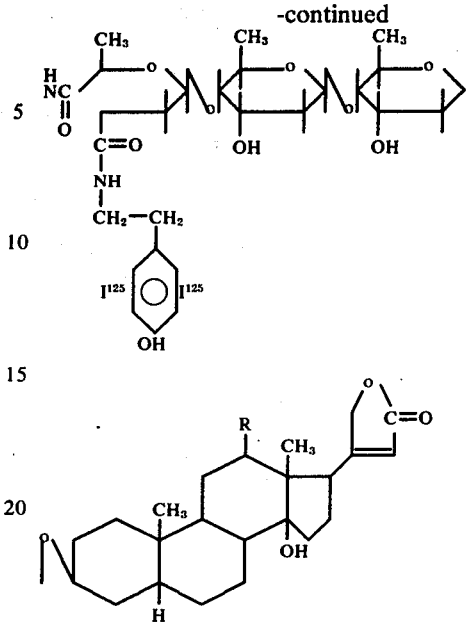

What is claimed is:
1. A compound of the formula:

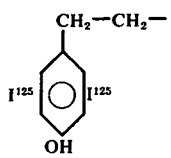

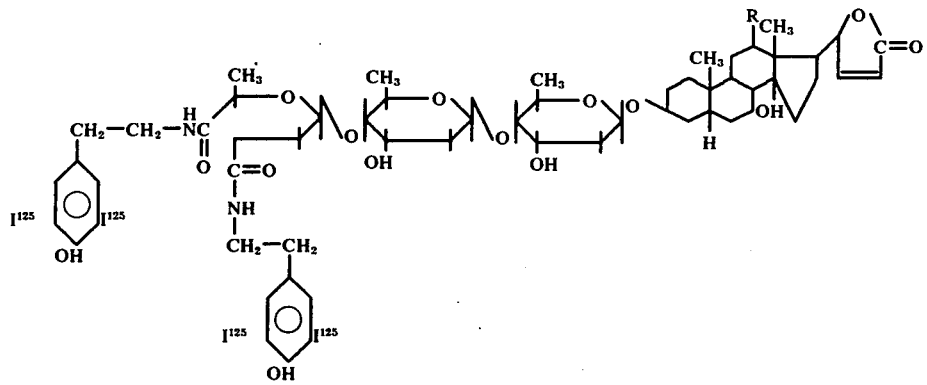

wherein R is selected from the group consisting of hydrogen and hydroxyl.

2. A process of synthesizing tetra-$^{125}$Iodo-di-tyramine derivatives of digitalis having the formula:

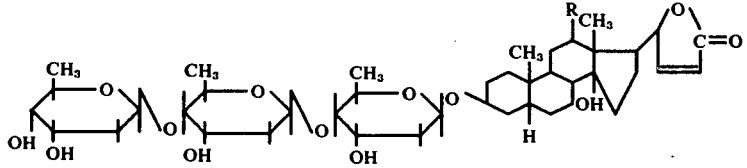

wherein R is hydrogen or hydroxyl, which consists essentially of the steps
reacting a derivative of digitalis having the formula wherein R is as above,
with a reagent selected from the group consisting of periodate and its sodium and potassium salts, lead tetra-acetate, aryl iodosoacetate, manganicpyrophosphate and sodium bismuthate,
to form the hemialdal of the digitalis derivative,
reacting the hemialdal of the digitalis derivative with a reagent selected from the group consisting of an amoniacal silver nitrate solution (Tollen's reagent), an alkaline copper II solution containing tartrate (Fehling's solution), a copper citrate complex (Benedict's solution), alkaline solutin of potassium mercuric oxide, bromine, iodine, N-bromosuccinimides, Mercury II oxide, Vanadium V, Chromium VI, Manganese III, permanganate in acid or alkali, manganese dioxide, cobalt, cerium, nickel peroxide in alkaline solution, nitric acid, benzoyl peroxide, bensenediazoacetate, lead tetraacetate, organic peroxyacids and ruthenium tetroxide, to form the dicarboxylic acid of the digitalis derivative, reacting the di-carboxylic acid of the digitalis derivative with tyramine and a reagent selected from the group consisting of carbodiimides, acid chlorides, acid azides, mixed anhydrides to form the di-tyramine of the digitalis derivative, reacting the di-tyramine of the digitalis derivative with chloramine T and radioactive iodide to form tetra$^{125}$Iodo-di-tyramine derivatives of digitalis.

3. The process as defined in claim 2 wherein R is hydroxyl and the digitalis derivative is digoxin.

4. The process as defined in claim 3 wherein digoxin is reacted with periodate to form digoxin hemialdal.

5. The process as defined in claim 4 wherein the digoxin hemialdal is reacted with Tollen's reagent to form digoxin di-carboxylic acid.

6. The process as defined in claim 5 wherein digoxin di-carboxylic acid is reacted with a carbodiimide selected from the group comprising N-ethyl-N'-(2 morpholinylithyl)-carbodiimide-metho-p-toluenesulfonate, and N,N'-dicyclohexylcarbodiimide, N-(3-dimethylaminopropyl)-N'-t-butylcarbodiimide N-ethyl-N'-(2-morpholinyl-ethyl)-carbodiimide.

7. The process as defined in claim 5 wherein said carbodiimide is 1-cyclohexyl-3-(2-morpholinoethyl)-carbodiimide metho-p-tulenesulfonate.

* * * * *